United States Patent
Hoyme et al.

(10) Patent No.: US 6,518,465 B2
(45) Date of Patent: Feb. 11, 2003

(54) REACTIVE DISTILLATION PROCESS FOR HYDROLYSIS OF ESTERS

(75) Inventors: Craig Alan Hoyme, Kingsport, TN (US); Edwin Franklin Holcombe, III, Cogan Station, PA (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/976,764

(22) Filed: Oct. 13, 2001

(65) Prior Publication Data

US 2002/0077501 A1 Jun. 20, 2002

Related U.S. Application Data

(60) Provisional application No. 60/240,756, filed on Oct. 16, 2000.

(51) Int. Cl.[7] .......................... C07C 41/00; C07C 43/00
(52) U.S. Cl. ..................... 568/698; 568/907; 562/607; 562/608
(58) Field of Search .............................. 562/607, 608; 568/698, 907

(56) References Cited

U.S. PATENT DOCUMENTS

| | | |
|---|---|---|
| 4,595,785 A | 6/1986 | Brake |
| 5,113,015 A | 5/1992 | Palmer et al. |
| 5,403,964 A * | 4/1995 | Saleh et al. |
| 5,770,770 A | 6/1998 | Kim et al. |

OTHER PUBLICATIONS

W. Song, G. Venimadhavan, J. M. Manning, M. F. Malone, and M. F. Doherty, Measurement of Residue Curve Maps and Heterogeneous Kinetics in Methyl Acetate Synthesis, Ind. Eng. Chem. Res., 1998, pp. 1917–1928, vol. 37, No. 5, American Chemical Society, U.S.

G. Venimadhavan, M. F. Malone, and M. F. Doherty, "Bifurcation Study of Kinetic Effects in Reactive Distillation", AlChE Journal, 1999, pp. 546–556, vol. 45, No. 3, U.S.

A. Nisoli, M. F. Malone, and M. F. Doherty, "Attainable Regions for Reaction with Separation", AlChE Journal, 1997, pp. 374–387, vol. 43, No. 2, U.S.

G. G. Podrebarac, F. F. T. NG and G. L. Rempel, "More uses for Catalytic Distillation", Chemtech, 1997, pp. 37–45, American Chemical Society, U.S.

Y. W. Kang and Y. Y. Lee, "Vapor–Liquid Equilibria with Chemical Reaction Equilibrium –Systems Containing Acetic Acid, Ethyl Alcohol, Water, and Ethyl Acetate–", Journal of Chemical Engineering of Japan, 1992, pp. 649–655, vol. 25, No. 6, Japan.

Kirk–Othmer, *Encyclopedia of Chemical Technology*, 4 ed., vol. 24, p. 980.

Y. Fuchigami, "Hydrolysis of Methyl Acetate in Distillation Column Packed with Reactive Packing of Ion Exchange Resin", Journal of Chemical Engineering of Japan, 1990, pp. 354–358, vol. 23, No. 3, Japan.

D. Barbosa and M. Doherty, "Design and Minimum–Reflux Calculations for Double–Feed Multicomponent Reactive Distillation Columns", 1988, pp. 2377–2389, vol. 43, No. 9, Chemical Engineering Science, Great Britain.

D. Barbosa and M. F. Doherty, "Design and Minimum–Reflux Calculations for Single–Feed Multicomponent Reactive Distillation Columns", 1988, pp. 1523–1537, vol. 43, No. 7, Chemical Engineering Science, Great Britain.

(List continued on next page.)

*Primary Examiner*—Deborah D. Carr
(74) *Attorney, Agent, or Firm*—Jonathan Wood; Bernard Graves, Jr.

(57) ABSTRACT

A process for hydrolyzing an alkyl ester to produce a carboxylic acid product and an ether product, the process includes the steps of introducing into a reaction zone of a reactive distillation column a feed containing the alkyl ester wherein the reaction zone is at a temperature and pressure to preferentially produce an ether from the ester; and recovering the ether and the carboxylic acid.

23 Claims, 5 Drawing Sheets

OTHER PUBLICATIONS

S. Ung and M. F. Doherty, "Calculation of Residue Curve Maps for Mixtures with Multiple Equilibrium Chemical Reactions", Ind. Eng. Chem. Res., 1995, pp. 3195–3202, American Chemical Society, U.S.

M. J. Okasinski and M. F. Doherty, "Thermodynamic Behavior of Reactive Azeotropes", AlChE Journal, 1997, pp. 2227–2238, vol. 43, No. 9, U.S.

A. Fredenslund, R. L. Jones, and J. M. Prausnitz, "Group–Contribution Estimation of Activity Coefficients in Nonideal Liquid Mixtures", AlChE Journal, 1975, pp. 1086–1099, vol. 21, No. 6, U.S.

H. K. Hansen, P. Rasmussen, A. Fredenslund, M. Schiller and J. Gmehling, "Vapor–Liquid Equilibria by UNIFAC Group Contribution. 5. Revision and Extension", Ind. Eng. Chem. Res. 1991 pp. 2352–2355, vol. 30, America Chemical Society U.S.

V. H. Agreda, L. R. Partin and W. H. Heise, "High–Purity Methyl Acetate Via Reactive Distillation", Chemical Engineering Process, 1990, pp. 40–46.

D. Barbosa and M. F. Doherty, "The Simple Distillation of Homogeneous Reactive Mixtures", Chemical Engineering Science, 1988, pp. 541–550, vol. 43, No. 3, Great Britain.

G. Buzad And M. F. Doherty, "Design of Three–Component Kinetically Controlled Reactive Distillation Columns Using Fixed–Point Methods", Chemical Engineering Science, 1994, pp. 1947–1963, vol. 49, No. 12, Great Britain.

N. Chadda, M. F. Doherty and M. F. Malone, "Effect of Chemical Kinetics on Feasible Splits for Reactive Distillation", AlChE Journal, 2001, pp. 590–601, vol. 47, No. 3, U.S.

F. Chen, R. S. Huss, M. F. Malone, M. F. Doherty, "Simulation of Kinetic Effects in, Reactive Distillation", Computers and Chemical Engineering, 2000, pp. 2457–2472, Elsevier Science Ltd., U.S.

J. L. Degarmo, V. N. Parulecker, and V. Pinjala, "Consider Reactive Distillation", Chemical Engineering Process, 1992, pp. 43–50.

M. F. Doherty and M. F. Malone, Conceptual Design of Distillation Systems, Reactice Distillation, chapter 10, 2001, p. 479, 487, McGraw–Hill Higher Education, U.S.

G. A. F. Fien and Y. A. Liu, "Heuristic Synthesis and Shortcut Design of Separation Process Using Residue Curve Maps: A Review", Ind. Eng. Chem. Res., 1994, pp. 2505–2522, vol. 33, American Chemical Society, U.S.

S. J. Han, Y. Jin and Z. Q. Yu, "Application of Fluidized Reaction–Distillation Column for Hydrolysis of Methyl Acetate", Chemical Engineering Journal, 1997, vol. 66, pp. 227–230, Elsevier Science S.A.

Kirk–Othmer, *Encyclopedia of Chemical Technology*, 4 ed., 1997, p. 980, vol. 24, John Wiley and Sons, U.S. and Canada.

W. Liang, Z. Wang, Y. Jin, Z. Yu and S. Yang," Performance of a Three–Phase Fluidized Bed as a Reactive Distillation Device", Chem. Eng. Techol., 1996, pp. 456–461, vol. 19.

T. Popken, L. Gotze, and J. Gmehling, "Reaction Kinetics and Chemical Equilibrium of Homogeneously and Heterogeneously Catalyzed Acetic Acid Esterification with Methanol and Methyl Acetate Hydrolysis", Ind. Eng. Chem. Res., 2000, pp. 2601–2611, American Chemical Society, U.S.

T. Popken, S. Steinigeweg, And J. Gmehling, "Synthesis and Hydrolysis of Methyl Acetate by Reactive Distillation Using Structured Catalytic Packings: Experiments and Simulation", Ind. Eng. Chem. Res., 2001, pp. 1566–1574, vol. 40, American Chemical Society, U.S.

W. Song, R. S. Huss, M. F. Doherty and M. F. Malone, "Discovery of a Reactive Azeotropes", Nature, 1997, pp. 561–563, vol. 388, U.S.

S. Ung and M. F. Doherty, "Synthesis of Reactive Distillation Systems with Multiple Equilibrium Chemical Reactions", Ind. Eng. Chem. Res., 1995, pp. 2555–2565, vol. 34, American Chemical Society, U.S.

D. B. Van Dongen and M. F. Doherty, "Design and Synthesis of Homogeneous Azeotropic Distillations. 1. Problem Formulation for a Single Column", Ind. Eng. Chem. Fundam., 1985, pp. 454–463, vol. 24, American Chemical Society, U.S.

J. Wang, X. GE, Z. Wang and Y. Jin, "Experimental Studies on the Catalytic Distillation for Hydrolysis of Methyl Acetate", Chem. Eng. Techol., 2001, pp. 155–159, vol. 24, No. 2.

P. N. Lodal, "Acetic Acid and its Derivatives", Production Economics, 1993, pp. 61–69, vol. 49, Marcel Dekker, U.S.

J. J. Siirola, "An Industrial Perspective on Process Synthesis", AIChE Symposium Series, 1995, pp. 222–233, vol. 91, U.S.

S. Ung and M. F. Doherty, "Synthesis of Reactive Distillation Systems with Multiple Equilibrium Chemical Reactions," Ind. Eng. Chem. Res., 1995, pp. 2555– 2565, vol. 34, American Chemical Society, U.S.

* cited by examiner

REACTIVE DISTILLATION PROCESS FOR HYDROLYSIS OF ESTERS

CROSS REFERENCE TO RELATED APPLICATIONS

Benefit is claimed to the earlier filed application having U.S. Ser. No. 60/240,756 filed Oct. 16, 2000, the entire disclosure of which is incorporated herein by reference.

BACKGROUND OF THE INVENTION

1. Field of the Invention

The present invention relates to a method for the hydrolysis of a lower alkyl ester to produce a carboxylic acid and corresponding alkyl ether using reactive distillation. The present invention is particularly useful for hydrolysis of methyl acetate to form dimethyl ether and acetic acid.

2. Background of the Invention

Methyl acetate is produced in great amounts as a byproduct from purified terephthalic acid (PTA) plants and polyvinyl alcohol (PVOH) plants. Since methyl acetate is a less valuable solvent, methyl acetate is sold at a low price or hydrolyzed to methanol and acetic acid, which are more valuable, by a hydrolysis reaction followed by conventional distillation processes. Conventional distillation after reaction, however, has some drawbacks. First of all, this complex process has low reactor yield due to the small equilibrium constant which governs the hydrolysis reaction. This requires a large recycle stream of methyl acetate.

TABLE I

| Component | Boiling Point, °C. (P = 1 atm) | Mole Fraction |
|---|---|---|
| Acetic Acid | 118.0 | — |
| Methanol | 64.5 | — |
| Methyl Acetate | 57.1 | — |
| Water | 100.0 | — |
| Methyl Acetate/Water azeotrope | 55.9 | 0.92/0.08 |
| Methyl Acetate/Methanol azeotrope | 53.2 | 0.66/0.34 |

The methyl acetate mixtures from both PVA processes and from PTA processes have azeotropic mixtures of methyl acetate/methanol and methyl acetate/water as described in Table I. It is possible to improve methyl acetate hydrolysis by increasing the amount of water in the feed, since the reaction is an equilibrium reaction. However, any water added to the system must be removed later making the overall energy requirements of the system increase as the amount of water is increased. The large methyl acetate recycle along with the separations of methanol/water and water/acetic acid result in a large process heat requirement.

Another drawback is high fixed costs and high operating costs resulting from separated hydrolysis reactors and multiple distillation towers including extractive distillation columns and dehydration columns. Accordingly, the high capital and energy costs expected for the conventional process indicate that a new process for the hydrolysis of methyl acetate would be highly desirable.

To improve the conversion of methyl acetate to acetic acid and methanol and the separation of these materials from the methyl acetate feed stream and water, U.S. Pat. No. 5,113,015 issued to Palmer et al. on May 12, 1992, discloses a reactive distillation process whereby methyl acetate is converted to acetic acid and methanol. The process includes contacting the methyl acetate with water in the presence of a catalyst packing material comprising a hydrolysis catalyst and a solvent comprising acetic acid to produce methanol and acetic acid, and coextensively, separating the methanol from the acetic acid.

Reactive distillation is a method to integrate reaction and distillation in the same column. Although reactive distillation has been known since the 1920s, most of the reaction and distillation processes have been independently operated. The advantages of the reactive distillation process for methyl acetate hydrolysis are more attractive than those of the conventional process, because integrating reaction and distillation technology in the same column reduces capital and operating costs greatly. Most hydrolysis or esterification reactions are limited by chemical equilibrium, but the reactive distillation process can shift the equilibrium reaction forward by removing the products, acetic acid and methanol, continuously from the reactants, methyl acetate and water. In cases where an azeotropic mixture is formed in the column, reactive distillation can break azeotropic compositions resulting in an increase in reaction yield and selectivity.

U.S. Pat. No. 5,770,770 issued to Kim et al. on Jun. 23, 1998 discloses a reactive distillation process for producing acetic acid and methanol as hydrolysis products from a byproduct composition containing more than 50% of methyl acetate. The process includes (a) hydrolyzing a mixture containing methyl acetate to acetic acid and methanol in a reaction zone, wherein ion exchange resin packing is present in the reaction zone as a catalyst, water is supplied downwardly to the ion exchange resin packing and the methyl acetate mixture is supplied upwardly to the ion exchange resin packing, (b) collecting unreacted methyl acetate and water vapor occupying the upper part of the reaction zone, condensing and returning them to the reaction zone, and (c) at the same time as step (b), collecting a reaction mixture from step (a) occupying the lower part of the reaction zone, separating the reaction mixture into the hydrolysis products and impurities by reboiling, returning the impurities to the reaction zone and recovering the hydrolysis products.

A problem with the aforementioned reactive distillation processes in converting methyl acetate to acetic acid and methanol is that large feed ratios of water/methyl acetate are required. This large amount of water in the bottoms product has to be separated from the desired acetic acid in one of the separation columns which results in increased heat requirements and capital costs.

Another problem with the aforementioned reactive distillation processes in converting methyl acetate to acetic acid and methanol is that large amounts of unreacted methyl acetate and water in the distillate must be condensed and returned to the reaction portion of the distillation column as well as reboiling a substantial amount of water from the bottoms. This substantially adds to the cost of energy and equipment.

Accordingly, there still exists a need for an improved process for the hydrolysis of methyl acetate.

SUMMARY OF THE INVENTION

As described above, a low equilibrium constant ($K_{eq} \approx 0.14$) and the presence of interfering azeotropes inhibit the hydrolysis of methyl acetate via conventional processes. Surprisingly, it has now been found that the problems previously associated with the hydrolysis of methyl acetate to form acetic acid and methanol can be overcome by preferentially driving the hydrolysis of the alkyl ester to form a carboxylic acid and an ether. In the case of methyl acetate, the products are acetic acid (bottoms) and dimethyl ether (distillate), which can be produced by the dehydration of methanol by using an alumina catalyst disclosed in U.S. Pat. No. 4,595,785, the entire disclosure of which is incorporated herein by reference. Accordingly, the process of the present invention is for hydrolyzing an alkyl ester to produce a carboxylic acid and an ether. The process includes the steps of introducing into a reaction zone of a reactive distillation column a feed containing the alkyl ester wherein the reaction zone of the distillation column is at a temperature and pressure that preferentially produces an ether from the ester; and recovering the ether.

From the description that follows, one skilled in the art will understand that, while the invention focuses on the hydrolysis of methyl acetate, the invention may be useful for the hydrolysis of other esters in which the corresponding ether has a lower boiling point than other components and preferably the azeotropes within the system.

It is an object of the present invention to provide a method for the hydrolysis of an alkyl ester to form a carboxylic acid and an ether.

It is another object of the present invention to provide a method for the hydrolysis of methyl acetate to form dimethyl ether and acetic acid.

BRIEF DESCRIPTION OF THE DRAWINGS

These and other objects and advantages of the present invention will become more apparent to those skilled in the art in view of the following description and the accompanying drawings. It is to be understood that the inventive concept is not to be considered limited to the constructions disclosed herein but instead by the scope of the appended claims.

DETAILED DESCRIPTION OF THE INVENTION

Figure 1:
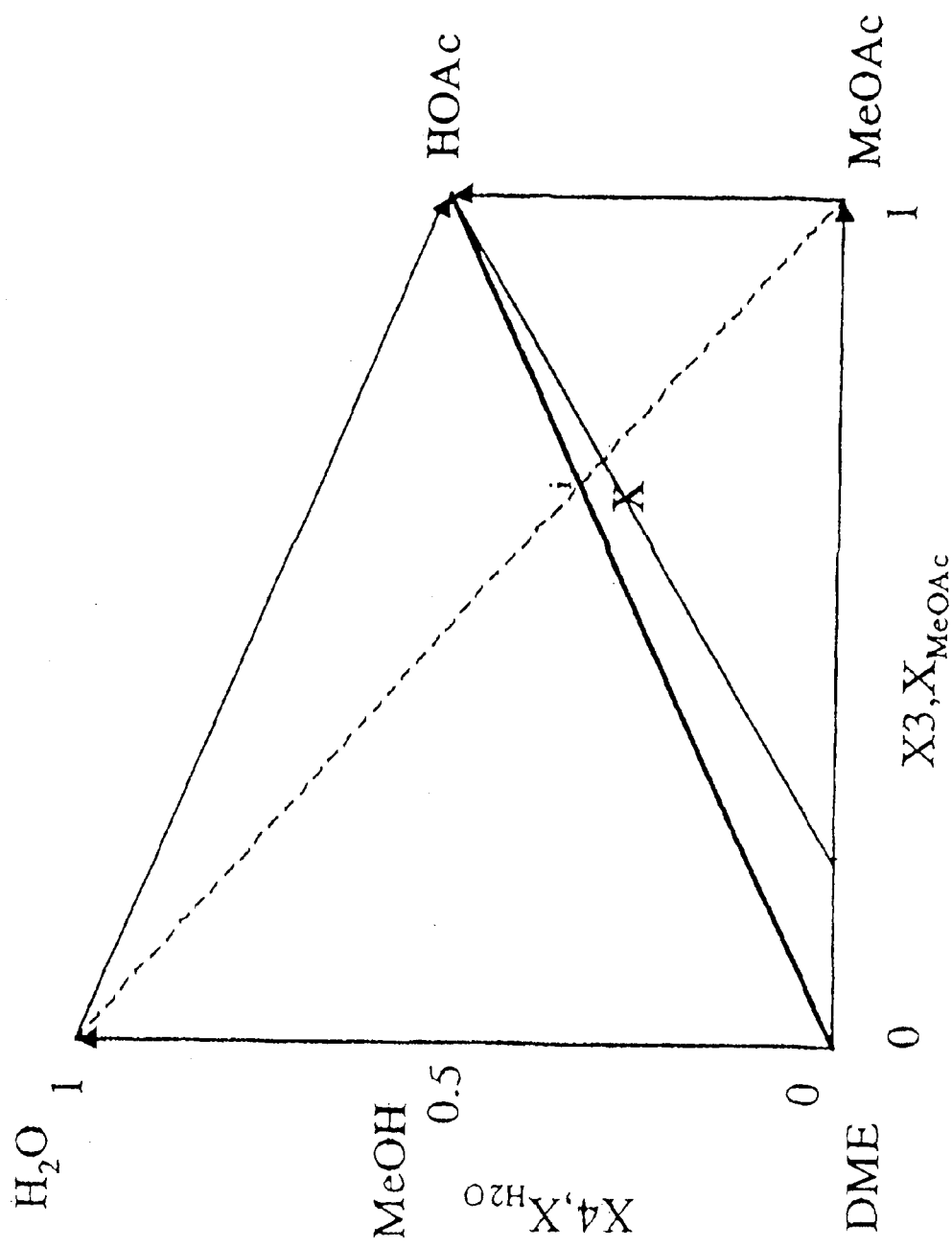
FIG. 1 is a transformed component space representation of a feasible reactive distillation design for this process for an indirect split with methyl acetate, methanol, and water present in the process feed stream.

As noted above, the present invention is a method for hydrolyzing an alkyl ester to a carboxylic acid and an ether utilizing reactive distillation. Although the present invention will be described in relation to methyl acetate and dimethyl ether, one skilled in the art will particularly understand the applicability of the present invention to the hydrolysis of alkyl esters having an alkyl group with 1 to 3 carbon atoms and particularly to equilibrium-limited reactions and the separation of azeotropic mixtures. As used herein, the term "alkyl ester" or "alkyl esters" means esters having an alkyl group with 1 to 3 carbon atoms. In the most preferred embodiment, the alkyl ester is methyl acetate, the carboxylic acid is acetic acid and the ether is dimethyl ether.

Reactive distillation is a method to integrate reaction and distillation in the same column. The reactive distillation column has three zones: (a) a rectifying zone where unreacted methanol, water, and methyl acetate are returned to the reactive zone and separated from the desired ether product; (b) a reaction zone; and (c) a stripping zone where methyl acetate, water and methanol are returned to the reaction zone and separated from the desired acetic acid bottoms product.

The reaction zone in the distillation column of the present invention includes an acid catalyst selected from a liquid catalyst such as sulfuric acid, phosphoric acid or a solid catalyst such as phosphoric acid-alumina catalyst, aluminotitanates, or other suitable strongly acidic ion exchange resins such as styrene and acrylic resins having sulfonic acid groups ($-SO_3H$) attached to an insoluble styrenic or acrylic polymer matrix, such as Amberlyst form ion exchange resin, (available from Dow Chemical Company) and mixtures thereof. In the case where a solid catalyst is utilized, the catalyst material can be wrapped in a non-reactive web or matrix material, such as fiberglass, and the resulting mat is rolled up with wire mesh between the layers to form a bale. At each level, the bales are arranged to cover the open area from the stack at the level below.

Alternatively, the solid resin is suitably sized so that the resin and, if so needed, from about 3 weight % to 30 weight %, based on the total weight of the polymer and resin, inert polymers can be molded together into a conventional packing shape, such as a Raschig ring, Berl saddle, Intalox saddle or Pall ring, using conventional molding processes known to those skilled in the art. The packing is then located or embedded in the reaction zone. The catalyst is installed in the reaction zone in a manner that there is sufficient interstitial space that the distillation column may be operated in either the gas or liquid phase.

The distillation column of the present invention can have one or more reactant feed points, with at least two feed points being preferred, i.e., an upper feed location for water and a lower feed location for methyl acetate mixtures. However, the utility of the present invention is not so limited, a feed stream may contain mixtures of the alkyl ester, the alkyl ether, lower aliphatic alcohol, water, and a corresponding carboxylic acid. The molar ratio of water to methyl acetate fed to the distillation column can range from about 0.05 to about 20 and preferably is from about 0.3 to about 3.

The number of theoretical stages or plates in the distillation column can be from about 10 to about 100 with from 0–10 plates in the rectifying zone, 5–25 plates in the reaction zone, and 0–40 plates in the stripping zone. Zero theoretical plates in the rectifying zone or stripping zone means no rectifying zone or stripping zone in the column layout.

In operation, a feed stream comprising an alkyl ester having from 1 to 3 carbon atoms in an alkyl group is introduced into the distillation column at a point that, depending upon the feed stream composition, is at the reaction zone, just above the reaction zone or just below the reaction zone. The reaction zone of the distillation column contains a packed or liquid catalyst material, such as that described above, which may be present in the form of one or more beds and optionally may contain one or more types of catalyst materials.

Desirably, the distillation column may have trays above the reaction zone and/or trays below the reaction zone. Alternatively, suitable conventional packing, such as Raschig rings, Pall rings, or saddles, may be used in place of trays in either the upper zone or the lower zone.

At least a portion of the alkyl ester is converted to the desired carboxylic acid and ether in the reaction zone. The lighter ether and other non-condensable material(s) pass up through the rectifying section of the distillation column while the carboxylic acid and other heavier material(s) pass down through the stripping section of the column. One skilled in the art will understand that an alkyl ester having more than 2 carbon atom in the alkyl group can be converted to the desired carboxylic acid and an alkene in the reaction zone instead of the ether if the column pressure and temperature are such that the alkene is preferred over the ether as a reaction product. The resulting alkene will then be the preferred distillate product of the ether.

In the case where methyl acetate is fed to the distillation column, some methyl acetate, methanol and water, may pass into a condensate drum where the condensed material is separated from the ether. The ether is removed from the system and the methyl acetate, methanol and water are returned to the distillation column for further reaction. The dimethyl ether distillate may then be hydrolyzed to form methanol in a separate vessel or a second reactive distillation column.

The heavier material, i.e., the higher-boiling carboxylic acid is passed from the stripping zone out of column. A portion of the material is passed through a reboiler and reintroduced into the distillation column.

In the case where the reactive distillation column is used to convert methyl acetate to dimethyl ether and acetic acid, the column is operated at a pressure ranging from about 2 psia (13.78 kPa) to about 600 psia (4,137 kPa) and preferably from about 100 psia (689.2 kPa) to about 300 psia (2068 kPa). The temperatures in the column depend upon the composition of the materials within the distillation column and the pressures. Since both the composition of the material on any particular stage, tray or section changes, the temperature at a certain location in the column is dictated by the composition and pressure at that location. Generally, the temperature within the distillation column ranges from about 30° C. to about 300° C. One skilled in the art will understand that the aforementioned temperatures and pressures are for the purpose of illustration only since such variables are dependent upon the feed composition as well as the size, type and configuration of the distillation column. Computation of actual operating parameters of a designed distillation column is within one skilled in the chemical engineering arts.

The low boiling component is now dimethyl ether (DME) and not methyl acetate or it's azeotropes. The addition of the side reaction to the hydrolysis of methyl acetate essentially accomplishes the desired characteristics of an alternative hydrolysis process so that reactive distillation can preferentially remove the DME and acetic acid from the reaction zone, thereby driving the complete conversion of methyl acetate. If methanol is desired, the DME product subsequently could be hydrolyzed back to methanol by the reaction:

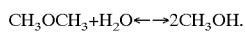

$$CH_3OCH_3 + H_2O \leftrightarrow 2CH_3OH.$$

The present invention is illustrated in greater detail by the specific examples presented below. It is to be understood that these examples are illustrative embodiments and are not intended to be limiting of the invention, but rather are to be construed broadly within the scope and content of the appended claims.

In the following examples, the process of the present invention was simulated using reactive distillation designs generated using AEA Technology's DISTIL 2.0.1 (Calgary, Canada), which is based on work from Doherty and Malone at the University of Massachusetts. Built-in literature for pure component and binary interaction physical properties was used to generate these initial designs. The Wilson-Dimer activity coefficient model was used to describe binary interactions. The Wilson-Dimer model allows for vapor phase association of carboxylic acids. The following designs assume that all stages are reactive and that sufficient catalyst is present to reach chemical equilibrium on every stage. Temperature-dependent equilibrium expressions were drawn from the publications by Nisoli, A.; Malone, M.; Doherty, M.; *AIChE J.* 1997, Feb, Vol. 43, No. 2, pp. 374–387, Song, W.; Venimadhavan, G.; Manning, J.; Malone, M.; Doherty, M.; *Ind. Eng. Chem. Res.* 1998, 37, pp. 1917–1928, and Doherty, M. F.; Malone, M. F, "Conceptual Design of Distillation Systems" McGraw Hill, N.Y., 2001, pp. 479–487, the disclosures of which are incorporated herein by reference in their entirety.

Aspen Plus Model Manager 10.1–0 (available from Aspen Technologies, Cambridge, Mass.) models were constructed using literature and in-house physical properties, with missing properties generated by the UNIFAC group contribution method. Such methodology is described in greater detail in A. Fredenslund, R. Jones and J. Prausnitz, "Group-Contribution Estimation of Activity Coefficients in Nonideal Liquid Mixtures", the disclosure of which is incorporated herein by reference. Activity coefficients were calculated using the Wilson-Nothnagel model, which allows for vapor phase association of carboxylic acids. As in the DISTIL 2.0.1 models, chemical equilibrium was assumed on every reactive stage, although not all stages were assumed to be reactive. Temperature-dependent equilibrium expressions were drawn from the publications discussed above. All examples below are the results of rigorous simulations.

EXAMPLE 1

A case was generated using ASPEN in which an excess of water was fed to the column, with essentially pure dimethyl ether taken overhead. This corresponds to a mass balance line such as line 1 of FIG. 4, with the solid line extending from the dimethyl ether corner (distillate) to the acetic acid/water edge (bottoms). The endpoints of the mass balance line represent potential compositions of the product streams.

The reactive distillation column was configured with 29 theoretical stages, with an equilibrium reactive zone (reactive stages with sufficient catalyst to approach chemical equilibrium) extending from stage 2 to stage 24. The Aspen simulation model's convention for stage numbering is for the condenser to be stage 1 and the reboiler is stage x, for a column with x stages. The simulated water feed was on stage 3 at a rate of 36 lb-mol/hr. The simulated methyl acetate feed was on stage 7 at a rate of 64 lbmol/hr. This gave a feed ratio for the column of 1:1.778 water:methyl acetate. The simulation was performed using a molar reflux ratio of 3.2 and a molar distillate-to-feed ratio of 0.32. The distillation column was at a pressure of 10 atmospheres (1013.3 kPa)

The distillation column did not have a rectifying section beyond the reactive zone. As shown in Table II, the distillate contains a dimethyl ether mole fraction of 0.99.

The stripping section of the column, stages 25–28, removes unreacted water, methanol, and methyl acetate from the bottoms product. Excess water is designed to be removed in the bottoms stream in order to produce purer dimethyl ether in the distillate. Unreacted water can be removed from the bottoms product using traditional separation methods and returned to the column feed if desired. The results of this simulation are in Table II below.

TABLE II

| Component | Distillate | Bottoms |
| --- | --- | --- |
| Acetic acid | $1.99 \times (10^{-5})$ | 0.934 |
| Methanol | 0.003 | $2.88 \times (10^{-4})$ |
| Methyl acetate | 0.004 | 0.005 |
| Water | 0.002 | 0.061 |
| Dimethyl ether | 0.991 | $6.74 \times (10^{-8})$ |
| Total flow (lb-mol/hr) | 32.0 | 68.0 |
| Temperature (° C.) | 45.3 | 207.5 |

As used herein "HOAc" is acetic acid; "MeOH" is methanol; "MeOAc" is methyl acetate; "H$_2$O" is water; and "DME" is dimethyl ether.

Figure 3:
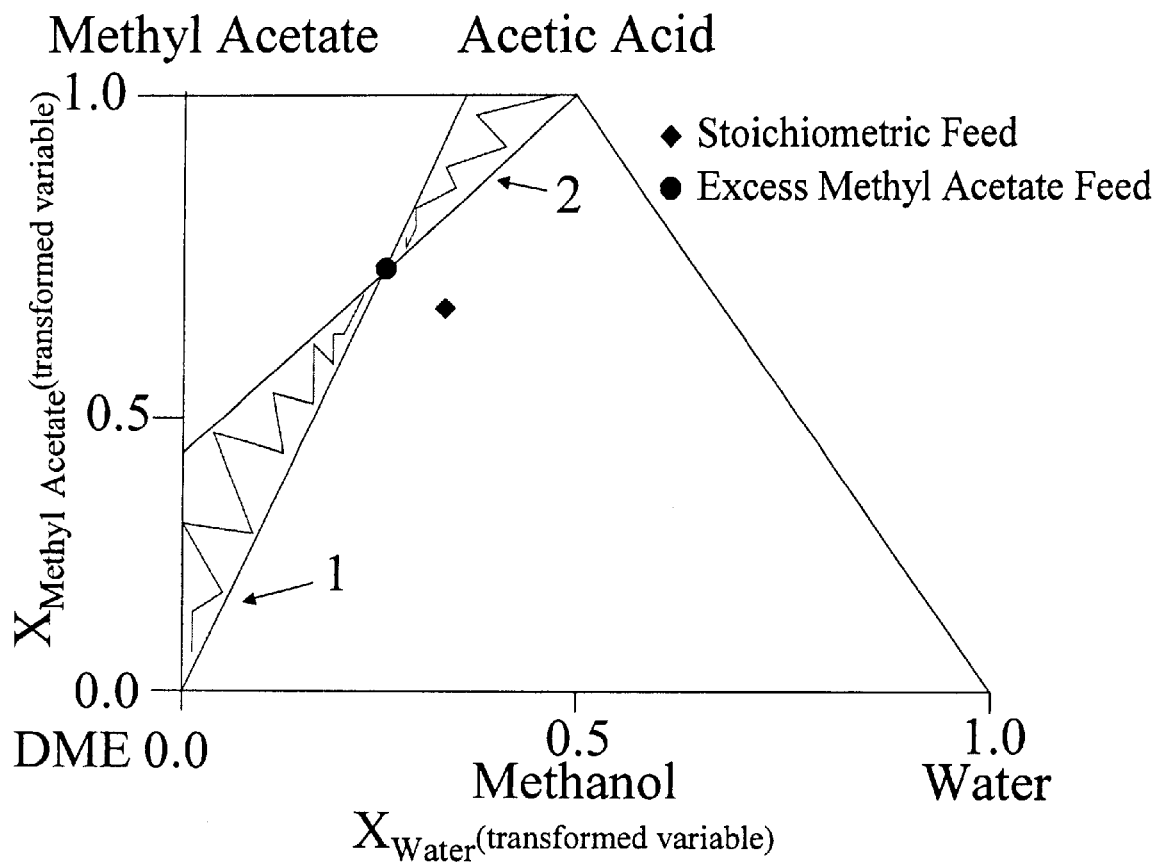
FIG. 3 is a plot illustrating the direct and indirect material balance lines for an excess of methyl acetate feed.

At a pressure of 10 atmospheres, the dimethyl ether reaction is significant. The potential products from a reactive distillation column can be more easily seen when the direct or indirect mass balance lines are drawn for a given column feed. The combination of the direct and indirect balance lines and all of the potential mass balances in-between can be shown by using the so-called bow-tie region, as shown in FIGS. 3 and 4.

Figure 2:
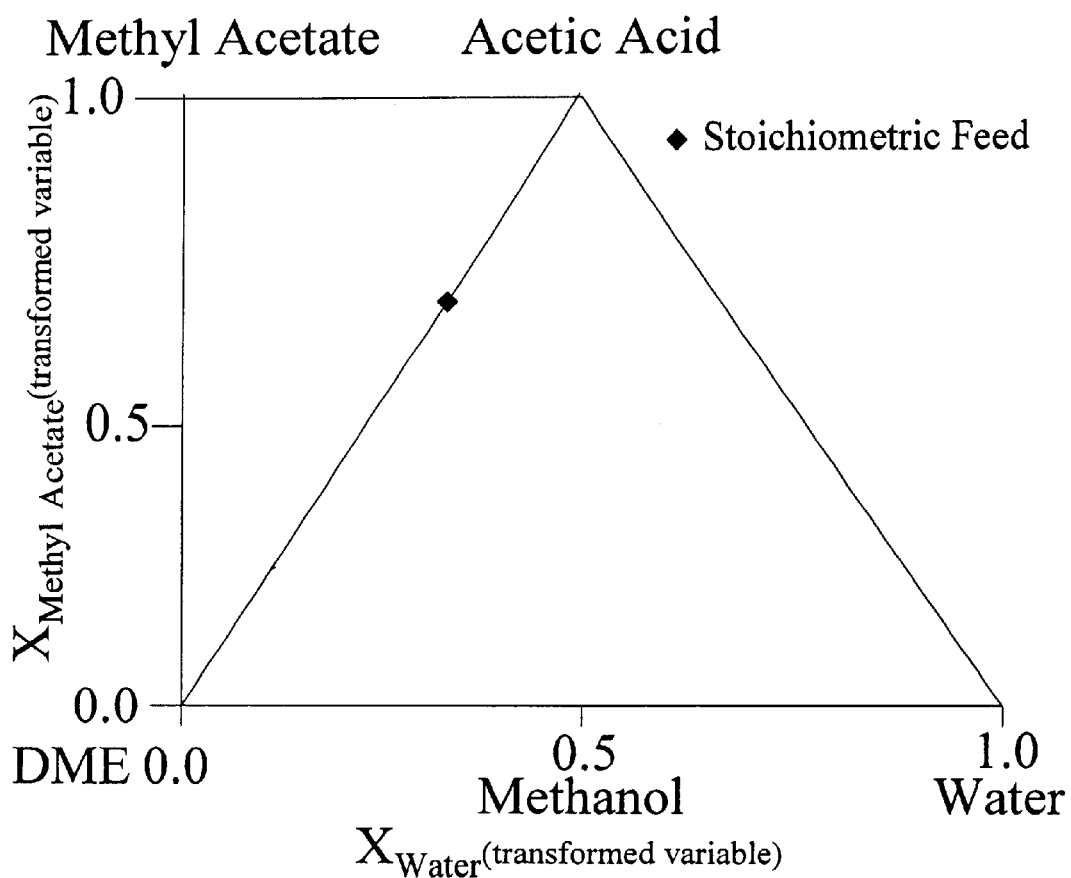
FIG. 2 is a plot of the material balance for a stoichiometric feed of methyl acetate and water at a reactor pressure of 10 atmospheres gauge.

FIG. 2 shows the material balance line for a stoichiometric feed of methyl acetate and water at a pressure of 10 atmospheres with DME as the distillate product and acetic acid as the bottoms product. FIG. 3 shows the direct (1) and indirect (2) material balance lines for an excess methyl acetate feed. The bow-tie region is the area between the direct and indirect material balance lines. This area describes the potential distillate and bottoms products. FIG. 4 shows the direct (1) and indirect (2) material balance lines for an excess water feed. The shown bow-tie region is a short-cut projection as the actual feasible distillate and bottoms products must lie on one of the residue curve lines going through both shaded regions shown on the reactive residue curve map. However, this short-cut projection can be extremely useful when evaluating the initial feasibility and design from a given RCM.

EXAMPLE 2

Figure 4:
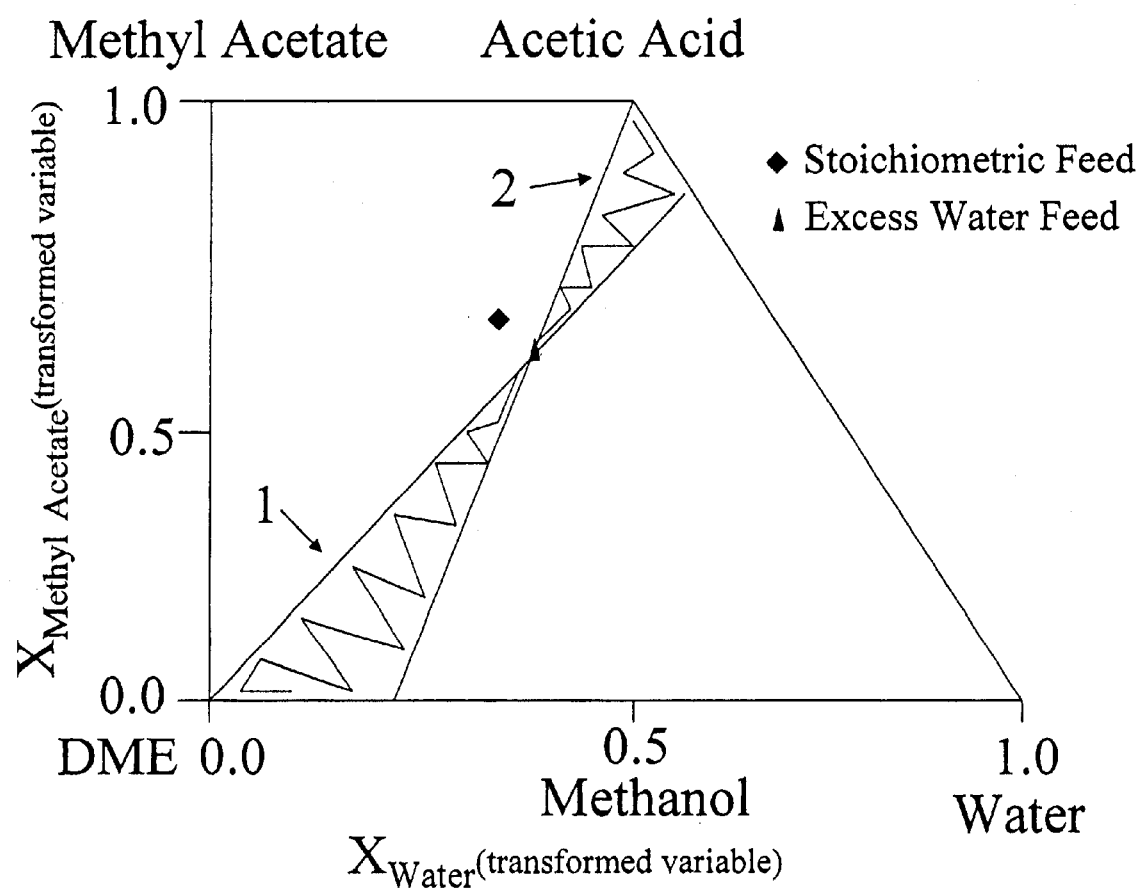
FIG. 4 is a plot illustrating the direct and indirect material balance lines for an excess of water feed.

Continuing referring to FIG. 4, a case was generated using ASPEN in which an excess of water was fed to the column, with essentially pure acetic acid taken as the bottoms product. This corresponds to mass balance line 2 with the solid line extending from the acetic acid corner (bottoms) to the dimethyl ether (DME)/methanol (MeOH)/water (H$_2$O) edge (distillate). The endpoints of the distillation line represent possible compositions of the product streams.

The reactive distillation column was configured with 70 theoretical stages, with an equilibrium reactive zone extending from stage 8 to stage 45. The simulated water feed was on stage 2 at a rate of 38 lb-mol/hr. The simulated methyl acetate feed was on stage 37 at a rate of 64 lb-mol/hr. This gave a feed ratio for the column of 1:1.684 water:methyl acetate. The simulation was performed using a molar reflux ratio of 2.05 and a molar distillate-to-feed ratio of 0.3726. The distillation column was at a pressure of 15 atmospheres (1519.9 kPa).

The distillation column had a rectifying section, stages 2–7, for separating unreacted water, methanol, and methyl acetate from the distillate product, improving the conversion of the reaction. The water excess is designed to be removed in the distillate in order to produce purer acetic acid in the bottoms stream. The unreacted water can be removed from the dimethyl ether product and returned to the column feed using traditional separation methods, if necessary.

The stripping section of the column, stages 46–69, removes unreacted water, methanol, and methyl acetate from the desired acetic acid bottoms product. The results of this simulation are in Table III below.

TABLE III

| Component | Distillate | Bottoms |
| --- | --- | --- |
| Acetic acid | $4.00 \times (10^{-6})$ | 0.978 |
| Methanol | 0.095 | $9.5 \times (10^{-8})$ |
| Methyl acetate | 0.038 | $2.0 \times (10^{-9})$ |
| Water | 0.092 | 0.022 |
| Dimethyl ether | 0.776 | trace |
| Total flow (lb-mol/hr) | 38.0 | 64.0 |
| Temperature (° C.) | 74.5 | 237.3 |

EXAMPLE 3

A case was generated using ASPEN in which an excess of methyl acetate was fed to the column, with essentially pure dimethyl ether taken overhead. This corresponds to a mass balance line such as line 1 of FIG. 3 with the solid line extending from the dimethyl ether corner (distillate) to the acetic acid/methyl acetate edge (bottoms). The endpoints of the distillation line represent potential compositions of the product streams The reactive distillation column was configured with 25 theoretical stages, with an equilibrium reactive zone extending from stage 7 to stage 18. The simulated water feed was on stage 7 at a rate of 32 lb-mol/hr. The simulated methyl acetate feed was on stage 11 at a rate of 70 lb-mol/hr. This gave a feed ratio for the column of 1:2.1875 water:methyl acetate. The simulation was performed using a molar reflux ratio of 4.9 and a molar distillate-to-feed ratio of 0.313. The distillation column was at a pressure of 10 atmospheres (1013.3 kPa).

The distillation column had a rectifying section, stages 2–6, for separating the DME product from unreacted methyl acetate, water, and methanol.

The stripping section of the column, stages 19–24, removes unreacted methanol, methyl acetate and water from the bottoms product. Excess methyl acetate is designed to be removed in the bottoms stream in order to produce purer DME in the distillate. Unreacted methyl acetate can subsequently be removed from the bottoms product using traditional separation methods and recycled to the column feed if desired. The results of this simulation are in Table IV below.

TABLE IV

| Component | Distillate | Bottoms |
| --- | --- | --- |
| Acetic acid | trace | 0.911 |
| Methanol | $1.18 \times (10^{-6})$ | $1.71 \times (10^{-6})$ |
| Methyl acetate | $1.48 \times (10^{-7})$ | 0.088 |
| Water | trace | 0.001 |
| Dimethyl ether | 0.999 | $2.05 \times (10^{-8})$ |
| Total flow (lb-mol/hr) | 31.9 | 70.1 |
| Temperature (° C.) | 44.9 | 206.0 |

EXAMPLE 4

A case was generated using ASPEN in which an excess of methyl acetate was fed to the column, with essentially pure acetic acid taken as the bottoms product. This corresponds to a mass balance line such as line 2 in FIG. 3 with the solid line extending from the acetic acid corner (bottoms) to the dimethyl ether/methyl acetate edge (distillate). The endpoints of the distillation line represent potential compositions of the product streams.

The reactive distillation column was configured with 25 theoretical stages, with an equilibrium reactive zone extending from stage 5 to stage 12. The simulated water feed was on stage 9 at a rate of 32 lb-mol/hr. The simulated methyl acetate feed was on stage 10 at a rate of 70 lb-mol/hr. This gave a feed ratio for the column of 1:2.1875 water:methyl acetate. The simulation was performed using a molar reflux ratio of 4.5 and a molar distillate-to-feed ratio of 0.3725. The distillation column was at a pressure of 10 atmospheres (1013.3 kPa).

The distillation column had a rectifying section, stages 2–4 for separating unreacted water, methanol and methyl acetate from the DME/excess MeOAc takeoff, improving the conversion of the reaction. The methyl acetate excess is designed to be removed in the distillate in order to produce purer acetic acid in the bottoms stream.

The stripping section of the column, stages 13–24, removes unreacted water, methanol and methyl acetate from the desired acetic acid bottoms product. The results of this simulation are in Table V below.

TABLE V

| Component | Distillate | Bottoms |
|---|---|---|
| Acetic acid | $1.56 \times (10^{-8})$ | 0.997 |
| Methanol | $4.30 \times (10^{-5})$ | $1.16 \times (10^{-7})$ |
| Methyl acetate | 0.160 | 0.002 |
| Water | $2.37 \times (10^{-8})$ | 0.001 |
| Dimethyl ether | 0.840 | trace |
| Total flow (lb-mol/hr) | 38.0 | 64.0 |
| Temperature (° C.) | 52.2 | 212.9 |

EXAMPLE 5

Referring to FIG. 1, a case was generated using ASPEN in which an excess of methyl acetate was fed to the column, with essentially pure acetic acid taken as the bottoms product. Additionally, methanol was fed along with the methyl acetate so that the mole fractions in the methyl acetate/methanol feed were $x_{MeOH}$ (mol)=0.102564 and $x_{MeOAc}$ (mol)=0.897436. This corresponds to a feed point such as (X), with the solid mass balance line extending from the acetic acid corner (bottoms) to the DME/MeOAc edge (distillate). The endpoints of the distillation line represent potential compositions of the product streams.

The reactive distillation column was configured with 27 theoretical stages, with an equilibrium reactive zone extending from stage 3 to stage 12. The simulated water feed was on stage 6 at a rate of 28 lb-mol/hr. The simulated methyl acetate and methanol feeds were on stage 7 at a rate of 70 lb-mol/hr. and 8 lb-mol/hr. respectively. This gave a feed ratio for the column of 1:2.5 $H_2O$:MeOAc. However, the methanol fed to the column will react to generate water, which is available to hydrolyze the methyl acetate fed to the column. If this water from reaction is considered part of the feed, the feed ratio of the column would be 1:2.1875 $H_2O$:MeOAc. The simulation was performed using a molar reflux ratio of 4.5 and a molar distillate-to-feed ratio of 0.39622. The distillation column was at a pressure of 10 atmospheres (1013.3 kPa).

The distillation column had a rectifying section, stage 2 for separating unreacted water, methanol, and methyl acetate from the DME/excess MeOAc takeoff, improving the conversion of the reaction. The methyl acetate excess is designed to be removed in the distillate in order to produce purer acetic acid in the bottoms stream. The unreacted methyl acetate can be removed from the DME product using traditional separation methods and returned to the column feed if desired.

The stripping section of the column, stages 13–26, removes unreacted water, methanol, and methyl acetate from the desired acetic acid bottoms product. The results of this simulation are in Table VI below.

TABLE VI

| Component | Distillate | Bottoms |
|---|---|---|
| Acetic acid | $4.62 \times (10^{-6})$ | 0.999 |
| Methanol | $1.19 \times (10^{-4})$ | $4.81 \times (10^{-9})$ |
| Methyl acetate | 0.143 | $1.44 \times (10^{-4})$ |
| Water | $1.41 \times (10^{-6})$ | $5.85 \times (10^{-5})$ |
| Dimethyl ether | 0.857 | trace |
| Total flow (lb-mol/hr) | 42.0 | 64.0 |
| Temperature (° C.) | 51.4 | 213.1 |

EXAMPLE 6

Figure 5:
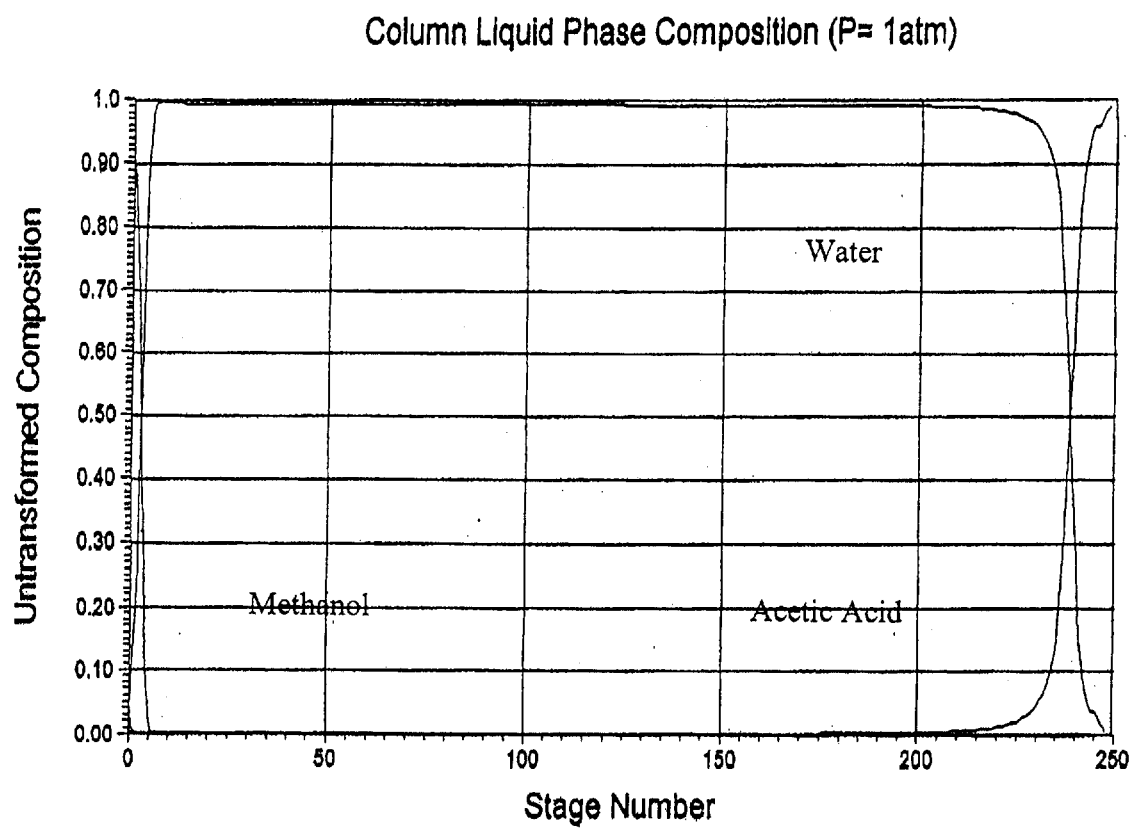
FIG. 5 illustrates for comparison purposes a theoretical column liquid phase composition operating at a pressure of 1 atmosphere gauge.

A case was generated running DISTIL 2.0.1 simulations at a pressure of one atmosphere and assuming thermodynamic and chemical equilibrium is obtained on every stage. Various solutions were found, but all simulations resulted in large reflux ratios and many theoretical stages as requirements for obtaining relatively pure acetic acid and methanol as the reactive distillation column products. Table VII and FIG. 5 present the results for a single stoichiometric feed of methyl acetate and water to a completely reactive distillation column.

TABLE VII

| | Mole Fractions | | |
|---|---|---|---|
| Component | Feed | Distillate | Bottoms |
| Water | 0.50 | 0.040758 | 0.010000 |
| Methyl Acetate | 0.50 | 0.049850 | 0.000100 |
| Acetic Acid | 0.00 | 0.000150 | 0.989900 |
| Methanol | 0.00 | 0.909242 | 0.000000 |

| Ratio (mol/mol) | | Trays | |
|---|---|---|---|
| Reflux | Reboil | Feed | Total |
| 120.0 | 131.8 | 245 | 249 |

Acetic acid can be obtained as the primary bottoms product. However, significant rectifying stages are required to obtain only a marginally pure methanol distillate product. This can be attributed to the fact that methanol is a saddle point and not the unstable node of this system. If excess water or methyl acetate were fed to the reactive distillation column, the number of stages could be reduced, but the excess reactant fed to the column would be found in the distillate or bottoms products, requiring further separation in an additional distillation column. It should be clear from this example and from the existing literature that it is very difficult to hydrolyze methyl acetate and obtain pure methanol and acetic acid from a reactive distillation column at operating atmospheric pressure.

EXAMPLE 7

A case was generated wherein a completely reactive distillation column was at a pressure of 10 atmospheres and had multiple feeds. Multiple feeds to the reactive distillation column typically improve selectivity, reactant conversion, or help in controlling column temperatures within certain ranges. Double feed reactive distillation columns were evaluated using DISTIL 2.0.1. Three different cases were evaluated: (1) a stoichiometric feed, (2) an excess water feed and (3) an excess methyl acetate feed. The computed results for these 3 cases appear in Tables VIII, IX and X, respectively.

The heavier reactant, water, was set as the top feed location (U) and lighter reactant, methyl acetate, as the lower feed location (L) and were delivered to the reactive distillation column at the feed ratio stated in the Tables below.

TABLE VIII

| Component | Mole Fractions | | | |
|---|---|---|---|---|
| | Feed (U) | Feed (L) | Distillate | Bottoms |
| Water | 1.00 | 0.00 | 0.007080 | 0.010000 |
| Methyl Acetate | 0.00 | 1.00 | 0.056948 | 0.000100 |
| DME | 0.00 | 0.00 | 0.927700 | 0.0 |
| Acetic Acid | 0.00 | 0.00 | 0.002836 | 0.989900 |
| Methanol | 0.00 | 0.00 | 0.005436 | 0.000000 |

| Ratio (mol/mol) | | Trays | | | Feed ratio |
|---|---|---|---|---|---|
| Reflux | Reboil | Feed (U) | Feed (L) | Total | (U/L) |
| 1 | 1.1 | 4 | 5 | 25 | 0.5 |

TABLE IX

| Component | Mole Fractions | | | |
|---|---|---|---|---|
| | Feed (U) | Feed (L) | Distillate | Bottoms |
| Water | 1.00 | 0.00 | 0.086342 | 0.010000 |
| Methyl Acetate | 0.00 | 1.00 | 0.003005 | 0.000100 |
| DME | 0.00 | 0.00 | 0.890481 | 0.000000 |
| Acetic Acid | 0.00 | 0.00 | 0.000567 | 0.989900 |
| Methanol | 0.00 | 0.00 | 0.019605 | 0.000000 |

| Ratio (mol/mol) | | Trays | | | Feed ratio |
|---|---|---|---|---|---|
| Reflux | Reboil | Feed (U) | Feed (L) | Total | (U/L) |
| 3.0 | 2.2 | 1 | 5 | 19 | 0.56 |

TABLE X

| Component | Mole Fractions | | | |
|---|---|---|---|---|
| | Feed (U) | Feed (L) | Distillate | Bottoms |
| Water | 1.00 | 0.00 | 0.000000 | 0.010000 |
| Methyl Acetate | 0.00 | 1.00 | 0.142410 | 0.000100 |
| DME | 0.00 | 0.00 | 0.850000 | 0.000000 |
| Acetic Acid | 0.00 | 0.00 | 0.007590 | 0.989900 |
| Methanol | 0.00 | 0.00 | 0.00000 | 0.000000 |

| Ratio (mol/mol) | | Trays | | | Feed ratio |
|---|---|---|---|---|---|
| Reflux | Reboil | Feed (U) | Feed (L) | Total | (U/L) |
| 0.95 | 1.1 | 5 | 6 | 25 | 0.47 |

The results of the above computer simulations of the process of the present invention indicate its feasibility and utility, particularly in the case to convert methyl acetate to acetic acid and dimethyl ether and avoid the aforementioned problems of prior art.

Having described the invention in detail, those skilled in the art will appreciate that modifications may be made to the various aspects of the invention without departing from the scope and spirit of the invention disclosed and described herein. It is, therefore, not intended that the scope of the invention be limited to the specific embodiments illustrated and described but rather it is intended that the scope of the present invention be determined by the appended claims and their equivalents.

We claim:

1. A process for preparing a carboxylic acid from an alkyl ester comprising:

a. introducing said alkyl ester into a reaction zone of a reactive distillation column wherein said reaction zone includes a catalyst and is at a pressure of from about 2 psia (13.78 kPa) to about 600 psia (4,137 kPa) and a temperature of from about 30° C. to about 300° C. to produce said carboxylic acid and an ether from said ester; and b. recovering said ether and said carboxylic acid.

2. The process of claim 1 wherein said alkyl ester is hydrolyzed in said reaction zone.

3. The process of claim 1 wherein said alkyl ester has from 1 to 3 alkyl carbon atoms.

4. The process of claim 1 wherein said alkyl ester is methyl acetate.

5. The process of claim 3 wherein said carboxylic acid is acetic acid and said ether is dimethyl ether.

6. The process of claim 5 further comprising hydrolyzing said recovered ether to form an alcohol.

7. The process of claim 6 wherein said alcohol is methanol.

8. The process of claim 1 wherein said reaction zone is at a pressure of from about 100 psia (689.2 kPa) to about 300 psia (2068 kPa).

9. A process for preparing a carboxylic acid from an alkyl ester having an alkyl group with 1 to 3 carbon atoms comprising:

a. introducing said alkyl ester into a reaction zone of a reactive distillation column wherein said reaction zone includes a catalyst and is at a pressure of from about 2 psia (13.78 kPa) to about 600 psia (4,137 kPa) and a temperature of from about 30° C. to about 300° C. to produce said carboxylic acid and an ether from said ester; and b. recovering said ether and said carboxylic acid.

10. The process of claim 9 wherein said alkyl ester is methyl acetate.

11. The process of claim 9 wherein said carboxylic acid is acetic acid and said ether is dimethyl ether.

12. The process of claim 9 wherein said reaction zone is at a pressure of from about 100 psia (689.2 kPa) to about 300 psia (2068 kPa) and a temperature of from about 30° C. to about 300° C.

13. The process of claim 9 further comprising hydrolyzing said recovered ether to form methanol.

14. The process of claim 10 wherein the molar ratio of water to methyl acetate is from about 0.05 to about 20.

15. The process of claim 14 wherein the molar ratio of water to methyl acetate is from about 0.3 to about 3.

16. A process for preparing acetic acid from methyl acetate comprising:
   a. introducing said methyl acetate into a reaction zone of a reactive distillation column wherein said reaction zone includes a catalyst and is at a pressure of from about 2 psia (13.78 kPa) to about 600 psia (4,137 kPa) and a temperature of from about 30° C. to about 300° C. to produce said acetic acid and dimethyl ether from said ester; and
   b. recovering said acetic acid and said dimethyl ether.

17. The process of claim 16 wherein said reaction zone is at a pressure of from about 100 psia (689.2 kPa) to about 300 psia (2068 kPa) and a temperature of from about 30° C. to about 300° C.

18. The process of claim 16 wherein the molar ratio of water to methyl acetate is from about 0.05 to about 20.

19. The process of claim 16 further comprising hydrolyzing said dimethyl ether to produce methanol.

20. The process of claim 9 wherein said catalyst is an acid catalyst.

21. The process of claim 9 wherein said acid catalyst is selected from the group consisting of sulfuric acid, phosphoric acid, phosphoric acid-alumina catalyst, aluminotitanates, styrene and acrylic resins having sulfonic acid groups ($-SO_3H$) attached to an insoluble styrenic or acrylic polymer matrix, and mixtures thereof.

22. The process of claim 16 wherein said catalyst is an acid catalyst.

23. The process of claim 16 wherein said acid catalyst is selected from the group consisting of sulfuric acid, phosphoric acid, phosphoric acid-alumina catalyst, aluminotitanates, styrene and acrylic resins having sulfonic acid groups ($-SO_3H$) attached to an insoluble styrenic or acrylic polymer matrix, and mixtures thereof.

* * * * *